(12) United States Patent
McNeel et al.

(10) Patent No.: US 7,635,753 B2
(45) Date of Patent: Dec. 22, 2009

(54) PROSTATE CANCER AND MELANOMA ANTIGENS

(75) Inventors: Douglas G. McNeel, Madison, WI (US); Edward J. Dunphy, Madison, WI (US); Jason A. Dubovsky, Tampa, FL (US); Luke H. Hoeppner, Minneapolis, MN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/033,229

(22) Filed: Feb. 19, 2008

(65) Prior Publication Data
US 2008/0206289 A1 Aug. 28, 2008

Related U.S. Application Data

(60) Provisional application No. 60/890,590, filed on Feb. 19, 2007.

(51) Int. Cl.
*C07K 14/00* (2006.01)
(52) U.S. Cl. ..................................... 530/350
(58) Field of Classification Search .................. 530/350
See application file for complete search history.

(56) References Cited

FOREIGN PATENT DOCUMENTS

WO   WO 00/00824 A1   1/2000

OTHER PUBLICATIONS

Dunphy et al (Journal of Clinical Immunology, Sep. 2004, 24(5): 492-502).*
Bradford T, et al., "Cancer immunomics: using autoantibody signatures in the early detection of prostate cancer," Urol. Oncol. 24:237-242 (2006).
Brinkmann U, et al., "Novel genes in the PAGE and GAGE family of tumor antigens found by homology walking in the dbEST database," Cancer Res. 59:1445-1448 (1999).
Chen Y, et al., "A testicular antigen aberrantly expressed in human cancers detected by autologous antibody screening," Proc. Natl. Acad. Sci. USA 94:1914-1918 (1997).
Chen Y, et al., "Identification of multiple cancer/testis antigens by allogeneic antibody screening of a melanoma cell line library," Proc Natl Acad Sci USA 95:6919-6923 (1998).
Chen M, et al., Isolation and characterization of PAGE-1 and GAGE-7. New genes expressed in the LNCaP prostate cancer progression model that share homology with melanoma-associated antigens, J. Biol. Chem. 273:17618-17625 (1998).
Crew A, et al., "Fusion of SYT to two genes, SSX1 and SSX2, encoding proteins with homology to the Kruppel-associated box in human synovial sarcoma," Embo. J. 14:2333-2340 (1995).
De Plaen E, et al., "Structure, chromosomal localization, and expression of 12 genes of the MAGE family," Immunogenetics 40:360-369 (1994).

Dong X, et al., "Identification of two novel CT antigens and their capacity to elicit antibody response in hepatocellular carcinoma patients," Br. J. Cancer 89:291-297 (2003).
Dunphy E, et al., "Identification of antigen-specific IgG in sera from patients with chronic prostatitis," J. Clin Immunol. 24:492-502 (2004).
Gure A, et al., "SSX: a multigene family with several members transcribed in normal testis and human cancer," Int. J. Cancer 72:965-971 (1997).
Hoeppner L, et al., "Humoral immune responses to testis antigens in sera from patients with prostate cancer," Cancer Immun. 6:1-7 (2006).
Kasahara M, et al., "A testis-specific gene Tpx-1 maps between Pgk-2 and Mep-1 on mouse chromosome 17," Immunogenetics 29:61-63 (1989).
Lee S, et al., "Immunomic analysis of human sarcoma," Proc Natl Acad Sci USA 100:2651-2656 (2003).
Lim S, et al., "Sperm protein 17 is a novel cancer-testis antigen in multiple myeloma," Blood 97:1508-1510 (2001).
Loriot A, et al., "Five new human cancer-germline genes identified among 12 genes expressed in spermatogonia," Int. J. Cancer 105:371-376 (2003).
Lurquin C, et al., "Two members of the human MAGEB gene family located in Xp21.3 are expressed in tumors of various histological origins," Genomics 46:397-408 (1997).
McNeel D, et al., "Antibody immunity to prostate cancer associated antigens can be detected in the serum of patients with prostate cancer," J. Urol. 164:1825-1829 (2000).
Mooney C, et al., "Identification of autoantibodies elicited in a patient with prostate cancer presenting as dermatomyositis," Inter. J. Urology 13:211-217 (2006).
Sasaki M, et al., "MAGE-E1, a new member of the melanoma-associated antigen gene family and its expression in human glioma," Cancer Res. 61:4809-4814 (2001).
Scanlan M, et al., "Identification of cancer/testis genes by database mining and mRNA expression analysis," Int. J. Cancer 98:485-492 (2002).
Van der Bruggen P, et al., "A gene encoding an antigen recognized by cytolytic T lymphocytes on a human melanoma," Science 254:1643-1647 (1991).
Van den Eynde B, et al., "A new family of genes coding for an antigen recognized by autologous cytolytic T lymphocytes on a human melanoma," J. Exp. Med. 182:689-698 (1995).

(Continued)

*Primary Examiner*—Sean E Aeder
(74) *Attorney, Agent, or Firm*—Quarles & Brady LLP

(57) ABSTRACT

Methods for identifying a human subject as a candidate for further prostate cancer or melanoma examination are disclosed. Also disclosed are methods for determining whether an immune therapy has elicited a tumor-specific immune response in a prostate cancer or melanoma patient. Further disclosed are kits that can be used to practice the above methods. Methods for identifying candidate compounds for further testing as preventive or therapeutic agents for melanoma are also disclosed.

1 Claim, 7 Drawing Sheets

OTHER PUBLICATIONS

Wang X, et al., "Autoantibody signatures in prostate cancer," N. Engl. J. Med. 353:1224-1235 (2005).

Yuan L, et al., "Isolation of a novel gene, TSP50, by a hypomethylated DNA fragment in human breast cancer," Cancer Res. 59:3215-3221 (1999).

Zendman A, et al., "CTp11, a novel member of the family of human cancer/testis antigens," Cancer Res. 59:6223-6229 (1999).

Scanlan, Matthew J. et al., "The Cancer/Testis Genes: Review, Standardization, and Commentary," Cancer Immunity 4:1 (2004).

Wagner, Claudia et al., "Identification of an HLA-A*02 Restricted Immunogenic Peptide Derived from the Cancer Testis Antigen HOM-MEL-40/SSx2," Cancer Immunity 3:18 (2003).

* cited by examiner

A

B

SEQUENCE LISTING

<160> NUMBER OF SEQ ID NOS: 56

<210> SEQ ID NO 1
<211> LENGTH: 29
<212> TYPE: DNA
<213> ORGANISM: ARTIFICIAL
<220> FEATURE:
<223> OTHER INFORMATION: PCR PRIMER

<400> SEQUENCE: 1
ggaattcatg tctcttgagc agaggagtc                                    29

<210> SEQ ID NO 2
<211> LENGTH: 31
<212> TYPE: DNA
<213> ORGANISM: ARTIFICIAL
<220> FEATURE:
<223> OTHER INFORMATION: PCR PRIMER

<400> SEQUENCE: 2
ccgctcgagc tcagactccc tcttcctcct c                                 31

<210> SEQ ID NO 3
<211> LENGTH: 21
<212> TYPE: DNA
<213> ORGANISM: ARTIFICIAL
<220> FEATURE:
<223> OTHER INFORMATION: PCR PRIMER

<400> SEQUENCE: 3
ggtgctcaaa taccagagaa g                                            21

<210> SEQ ID NO 4
<211> LENGTH: 22
<212> TYPE: DNA
<213> ORGANISM: ARTIFICIAL
<220> FEATURE:
<223> OTHER INFORMATION: PCR PRIMER

<400> SEQUENCE: 4
ctttgggtcc agatctctcg tg                                           22

<210> SEQ ID NO 5
<211> LENGTH: 28
<212> TYPE: DNA
<213> ORGANISM: ARTIFICIAL
<220> FEATURE:
<223> OTHER INFORMATION: PCR PRIMER

<400> SEQUENCE: 5
ggaattccat gcaggccgaa ggccgggg                                     28

<210> SEQ ID NO 6
<211> LENGTH: 31
<212> TYPE: DNA
<213> ORGANISM: ARTIFICIAL
<220> FEATURE:
<223> OTHER INFORMATION: PCR PRIMER

<400> SEQUENCE: 6
ccgctcgagc ttagcgcctc tgccctgagg g                                 31

<210> SEQ ID NO 7
<211> LENGTH: 31
<212> TYPE: DNA
<213> ORGANISM: ARTIFICIAL
<220> FEATURE:
<223> OTHER INFORMATION: PCR PRIMER

<400> SEQUENCE: 7
ggaattcatg agttggcgag gaagatcgac c                                 31

<210> SEQ ID NO 8
<211> LENGTH: 31
<212> TYPE: DNA

```
<213> ORGANISM: ARTIFICIAL
<220> FEATURE:
<223> OTHER INFORMATION: PCR PRIMER

<400> SEQUENCE: 8
ccgctcgagt taacactgtg agcttttcac c                                    31

<210> SEQ ID NO 9
<211> LENGTH: 28
<212> TYPE: DNA
<213> ORGANISM: ARTIFICIAL
<220> FEATURE:
<223> OTHER INFORMATION: PCR PRIMER

<400> SEQUENCE: 9
ggaattcatg aacggagacg acgccttg                                        28

<210> SEQ ID NO 10
<211> LENGTH: 31
<212> TYPE: DNA
<213> ORGANISM: ARTIFICIAL
<220> FEATURE:
<223> OTHER INFORMATION: PCR PRIMER

<400> SEQUENCE: 10
ccgctcgagt tactcgtcat cttcctcagg g                                    31

<210> SEQ ID NO 11
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 11
ccaattgatg tgctctactc taaagaagtg tg                                   32

<210> SEQ ID NO 12
<211> LENGTH: 35
<212> TYPE: DNA
<213> ORGANISM: ARTIFICIAL
<220> FEATURE:
<223> OTHER INFORMATION: PCR PRIMER

<400> SEQUENCE: 12
ccgctcgagt taggagattt gcttgaaggc ctctg                                35

<210> SEQ ID NO 13
<211> LENGTH: 33
<212> TYPE: DNA
<213> ORGANISM: ARTIFICIAL
<220> FEATURE:
<223> OTHER INFORMATION: PCR PRIMER

<400> SEQUENCE: 13
ggaattcaat ggctttacta ccggtgttgt ttc                                  33

<210> SEQ ID NO 14
<211> LENGTH: 34
<212> TYPE: DNA
<213> ORGANISM: ARTIFICIAL
<220> FEATURE:
<223> OTHER INFORMATION: PCR PRIMER

<400> SEQUENCE: 14
ccgctcgagt cagtaaattt tgttctcaca tagg                                 34
```

<210> SEQ ID NO 15
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 15
ggaattcatg gagagcccca aaagaagaa cc                                 32

<210> SEQ ID NO 16
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 16
ccgctcgagt taaacttgtt gctcttcacc tg                                32

<210> SEQ ID NO 17
<211> LENGTH: 30
<212> TYPE: DNA
<213> ORGANISM: ARTIFICIAL
<220> FEATURE:
<223> OTHER INFORMATION: PCR PRIMER

<400> SEQUENCE: 17
ggaattcatg caggccgaag gccggggcac                                   30

<210> SEQ ID NO 18
<211> LENGTH: 34
<212> TYPE: DNA
<213> ORGANISM: ARTIFICIAL
<220> FEATURE:
<223> OTHER INFORMATION: PCR PRIMER

<400> SEQUENCE: 18
ccgctcgagc taaatgagag gggcagagaa catc                              34

<210> SEQ ID NO 19
<211> LENGTH: 31
<212> TYPE: DNA
<213> ORGANISM: ARTIFICIAL
<220> FEATURE:
<223> OTHER INFORMATION: PCR PRIMER

<400> SEQUENCE: 19
ggaattcgat gagtgcacga gtgagatcaa g                                 31

<210> SEQ ID NO 20
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 20
ccgctcgagt tatggctgcc catccctgct tc                                32

<210> SEQ ID NO 21
<211> LENGTH: 32
<212> TYPE: DNA
<213> ORGANISM: ARTIFICIAL
<220> FEATURE:

<223> OTHER INFORMATION: PCR PRIMER

<400> SEQUENCE: 21
ccaattgcat ggctgaggga agcttcagcg tg                      32

<210> SEQ ID NO 22
<211> LENGTH: 31
<212> TYPE: DNA
<213> ORGANISM: ARTIFICIAL
<220> FEATURE:
<223> OTHER INFORMATION: PCR PRIMER

<400> SEQUENCE: 22
ccgctcgagt caacggtgct ggatccagga g                       31

<210> SEQ ID NO 23
<211> LENGTH: 33
<212> TYPE: DNA
<213> ORGANISM: ARTIFICIAL
<220> FEATURE:
<223> OTHER INFORMATION: PCR PRIMER

<400> SEQUENCE: 23
ccaattgatg gacaaacaat ccagtgccgg cgg                     33

<210> SEQ ID NO 24
<211> LENGTH: 37
<212> TYPE: DNA
<213> ORGANISM: ARTIFICIAL
<220> FEATURE:
<223> OTHER INFORMATION: PCR PRIMER

<400> SEQUENCE: 24
ccgctcgagc tactttgcag gtatttcaca ttatttc                 37

<210> SEQ ID NO 25
<211> LENGTH: 31
<212> TYPE: DNA
<213> ORGANISM: ARTIFICIAL
<220> FEATURE:
<223> OTHER INFORMATION: PCR PRIMER

<400> SEQUENCE: 25
ggaattcatg tggcgcgtct tgtttctgct c                       31

<210> SEQ ID NO 26
<211> LENGTH: 33
<212> TYPE: DNA
<213> ORGANISM: ARTIFICIAL
<220> FEATURE:
<223> OTHER INFORMATION: PCR PRIMER

<400> SEQUENCE: 26
cggctcgaga ctacccttta ggttcactct cac                     33

<210> SEQ ID NO 27
<211> LENGTH: 31
<212> TYPE: DNA
<213> ORGANISM: ARTIFICIAL
<220> FEATURE:
<223> OTHER INFORMATION: PCR PRIMER

<400> SEQUENCE: 27
ggaattcatg ggtcgctggt gccagaccgt c                       31

<210> SEQ ID NO 28
<211> LENGTH: 28
<212> TYPE: DNA
<213> ORGANISM: ARTIFICIAL
<220> FEATURE:
<223> OTHER INFORMATION: PCR PRIMER

<400> SEQUENCE: 28
ccgctcgagt cagagggcag caaggagg                                           28

<210> SEQ ID NO 29
<211> LENGTH: 34
<212> TYPE: DNA
<213> ORGANISM: ARTIFICIAL
<220> FEATURE:
<223> OTHER INFORMATION: PCR PRIMER

<400> SEQUENCE: 29
ggaattcatg tcttcacata ggaggaaagc gaag                                    34

<210> SEQ ID NO 30
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 30
ccgctcgagc tactcgtcac catgttcctc ac                                      32

<210> SEQ ID NO 31
<211> LENGTH: 31
<212> TYPE: DNA
<213> ORGANISM: ARTIFICIAL
<220> FEATURE:
<223> OTHER INFORMATION: PCR PRIMER

<400> SEQUENCE: 31
ggaattcatg gcaggaggcc ctcccaacac c                                       31

<210> SEQ ID NO 32
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 32
ccgctcgaga tcactggttc atccacagcc ac                                      32

<210> SEQ ID NO 33
<211> LENGTH: 28
<212> TYPE: DNA
<213> ORGANISM: ARTIFICIAL
<220> FEATURE:
<223> OTHER INFORMATION: PCR PRIMER

<400> SEQUENCE: 33
ggaattcgtg atgcaggcgc catgggcc                                           28

<210> SEQ ID NO 34
<211> LENGTH: 34
<212> TYPE: DNA
<213> ORGANISM: ARTIFICIAL
<220> FEATURE:
<223> OTHER INFORMATION: PCR PRIMER

```
<400> SEQUENCE: 34
ccgctcgagc tatagttgcc cttcacctgc ttgg                    34

<210> SEQ ID NO 35
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 35
ggaattcatg tctctacgct gcggggatgc ag                      32

<210> SEQ ID NO 36
<211> LENGTH: 39
<212> TYPE: DNA
<213> ORGANISM: ARTIFICIAL
<220> FEATURE:
<223> OTHER INFORMATION: PCR PRIMER

<400> SEQUENCE: 36
ccgctcgagt tttagaggtc ttttgttttt cttttagcc               39

<210> SEQ ID NO 37
<211> LENGTH: 31
<212> TYPE: DNA
<213> ORGANISM: ARTIFICIAL
<220> FEATURE:
<223> OTHER INFORMATION: PCR PRIMER

<400> SEQUENCE: 37
ccaattgatg tcgattccat tctccaacac c                       31

<210> SEQ ID NO 38
<211> LENGTH: 33
<212> TYPE: DNA
<213> ORGANISM: ARTIFICIAL
<220> FEATURE:
<223> OTHER INFORMATION: PCR PRIMER

<400> SEQUENCE: 38
ccgctcgagt cacttgtttt cctcttttc ctc                      33

<210> SEQ ID NO 39
<211> LENGTH: 31
<212> TYPE: DNA
<213> ORGANISM: ARTIFICIAL
<220> FEATURE:
<223> OTHER INFORMATION: PCR PRIMER

<400> SEQUENCE: 39
ggaattcatg cctcttgagc agaggagtca g                       31

<210> SEQ ID NO 40
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 40
ccgctcgaga ctcactcttc cccctctctc aa                      32

<210> SEQ ID NO 41
<211> LENGTH: 27
```

```
<212> TYPE: DNA
<213> ORGANISM: ARTIFICIAL
<220> FEATURE:
<223> OTHER INFORMATION: PCR PRIMER

<400> SEQUENCE: 41
ggaattcatg cctcggggtc agaagag                                        27

<210> SEQ ID NO 42
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 42
acgcgtcgac tcacatgggg tgggaggacc tg                                  32

<210> SEQ ID NO 43
<211> LENGTH: 31
<212> TYPE: DNA
<213> ORGANISM: ARTIFICIAL
<220> FEATURE:
<223> OTHER INFORMATION: PCR PRIMER

<400> SEQUENCE: 43
ggaattcatg cctcgtggtc agaagagtaa g                                   31

<210> SEQ ID NO 44
<211> LENGTH: 31
<212> TYPE: DNA
<213> ORGANISM: ARTIFICIAL
<220> FEATURE:
<223> OTHER INFORMATION: PCR PRIMER

<400> SEQUENCE: 44
ccgctcgagc tcagactccg gctttctctt c                                   31

<210> SEQ ID NO 45
<211> LENGTH: 29
<212> TYPE: DNA
<213> ORGANISM: ARTIFICIAL
<220> FEATURE:
<223> OTHER INFORMATION: PCR PRIMER

<400> SEQUENCE: 45
ggaattcatg tcttctgagc agaagagtc                                      29

<210> SEQ ID NO 46
<211> LENGTH: 30
<212> TYPE: DNA
<213> ORGANISM: ARTIFICIAL
<220> FEATURE:
<223> OTHER INFORMATION: PCR PRIMER

<400> SEQUENCE: 46
ccgctcgagc tcagactccc tcttcctcct                                     30

<210> SEQ ID NO 47
<211> LENGTH: 29
<212> TYPE: DNA
<213> ORGANISM: ARTIFICIAL
<220> FEATURE:
<223> OTHER INFORMATION: PCR PRIMER

<400> SEQUENCE: 47
```
ggaattcatg aacggagaca acacctttg                                    29

<210> SEQ ID NO 48
<211> LENGTH: 31
<212> TYPE: DNA
<213> ORGANISM: ARTIFICIAL
<220> FEATURE:
<223> OTHER INFORMATION: PCR PRIMER

<400> SEQUENCE: 48
ccgctcgagt tactcgtcat cttcctcagg g                                 31

<210> SEQ ID NO 49
<211> LENGTH: 31
<212> TYPE: DNA
<213> ORGANISM: ARTIFICIAL
<220> FEATURE:
<223> OTHER INFORMATION: PCR PRIMER

<400> SEQUENCE: 49
ggaattcatg agttggcgag gaagatcgac c                                 31

<210> SEQ ID NO 50
<211> LENGTH: 36
<212> TYPE: DNA
<213> ORGANISM: ARTIFICIAL
<220> FEATURE:
<223> OTHER INFORMATION: PCR PRIMER

<400> SEQUENCE: 50
ccgctcgagt taacactgtg attgcttttc accttc                            36

<210> SEQ ID NO 51
<211> LENGTH: 31
<212> TYPE: DNA
<213> ORGANISM: ARTIFICIAL
<220> FEATURE:
<223> OTHER INFORMATION: PCR PRIMER

<400> SEQUENCE: 51
ggaattcatg attgggccta tgcggcccga g                                 31

<210> SEQ ID NO 52
<211> LENGTH: 36
<212> TYPE: DNA
<213> ORGANISM: ARTIFICIAL
<220> FEATURE:
<223> OTHER INFORMATION: PCR PRIMER

<400> SEQUENCE: 52
ccgctcgagt taacactgtg attgcccttc accttc                            36

<210> SEQ ID NO 53
<211> LENGTH: 18
<212> TYPE: DNA
<213> ORGANISM: ARTIFICIAL
<220> FEATURE:
<223> OTHER INFORMATION: PCR PRIMER

<400> SEQUENCE: 53
gaggagcctg agcgaacg                                                18

<210> SEQ ID NO 54
<211> LENGTH: 31
<212> TYPE: DNA
<213> ORGANISM: ARTIFICIAL

```
<220> FEATURE:
<223> OTHER INFORMATION: PCR PRIMER

<400> SEQUENCE: 54
ggaattctta gtgccttctg catgttctct t                          31

<210> SEQ ID NO 55
<211> LENGTH: 25
<212> TYPE: DNA
<213> ORGANISM: ARTIFICIAL
<220> FEATURE:
<223> OTHER INFORMATION: PCR PRIMER

<400> SEQUENCE: 55
gaggatatga gatcagaaag agaag                                 25

<210> SEQ ID NO 56
<211> LENGTH: 23
<212> TYPE: DNA
<213> ORGANISM: ARTIFICIAL
<220> FEATURE:
<223> OTHER INFORMATION: PCR PRIMER

<400> SEQUENCE: 56
tccacactgc cagtgtggct cat                                   23
```

PROSTATE CANCER AND MELANOMA ANTIGENS

CROSS-REFERENCE TO RELATED APPLICATION

This application claims the benefit of U.S. Provisional Patent Application Ser. No. 60/890,590, filed Feb. 19, 2007, incorporated herein by reference as if set forth in its entirety.

STATEMENT REGARDING FEDERALLY SPONSORED RESEARCH OR DEVELOPMENT

This invention was made with United States government support awarded by the following agency: NIH K23 RR16489. The United States has certain rights in this invention.

BACKGROUND

Immune responses can be elicited to tumor-expressed antigens. For example, several groups have reported the detection of antibody responses to prostate tumor-associated antigens compared with control groups (Wang X, et al., N. Engl. J. Med. 353:1224-1235 (2005); McNeel D, et al., J. Urol. 164: 1825-1829 (2000); Minelli A, et al., Anticancer Res. 25:4399-4402 (2005); Bradford T, et al., Urol Oncol. 24:237-242 (2006); and Shi F, et al., Prostate 63:252-258 (2005)). Cancer-testis antigens (CTA) are of particular interest as potential tumor antigens given that their expression is typically restricted to germ cells among normal tissues, but aberrantly expressed in tumor cells (Scanlan M, et al., Cancer Immun. 4:1 (2004)). The absence of MHC class I molecule expression on germ cells makes CTA essentially tumor-specific antigens in terms of potential CD8$^+$ T-cell target antigens (Kowalik I, et al., Andrologia. 21:237-243 (1989)). Many of these CTA were discovered using antibody screening methods including the serological evaluation of recombinant cDNA expression libraries (SEREX) approach (Sahin U, et al., Proc. Natl. Acad. Sci. USA 92:11810-11813 (1005); Hoeppner L, et al., Cancer Immun. 6:1-7 (2006); and Tureci O, et al., Mol. Med. Today 3:342-349 (1997)).

Several CTA, including members of the MAGE and GAGE families, have been identified as antigens recognized by tumor-specific cytotoxic T-cells (CTL) (Van der Bruggen P, et al., Science 254:1643-1647 (1991); and Van den Eynde B, et al., J. Exp. Med. 182:689-698 (1995)). Detectable immune responses to these antigens are believed to be a result of their ectopic expression in MHC class I-expressing malignant cells. Several CTA have been shown to be recognized by both antibodies and CTL, thus providing validation for the original approach of using antibody screening to identify potential tumor-specific T cell antigens (Jäger E, et al., J. Exp. Med. 187:265-270 (1998); and Monji M, et al., Clin. Cancer Res. 10:6047-6057 (2004)). Some CTA are expressed in several malignancies of different tissue origins (Scanlan et al., supra; and Mashino K, et al., Br. J. Cancer. 85:713-720 (2001)).

BRIEF SUMMARY

The present invention provides methods for identifying a human subject as a candidate for further prostate cancer or melanoma examination based on certain prostate cancer and melanoma antigens identified by the inventors. Methods of identifying immune responses elicited by an immune therapy directed at prostate cancer or melanoma are also provided. The present invention also provides kits that can be used to practice the above methods. Methods for identifying candidate compounds for further testing as preventive or therapeutic agents for melanoma are also disclosed.

DETAILED DESCRIPTION OF PREFERRED EMBODIMENTS

Figure 1:
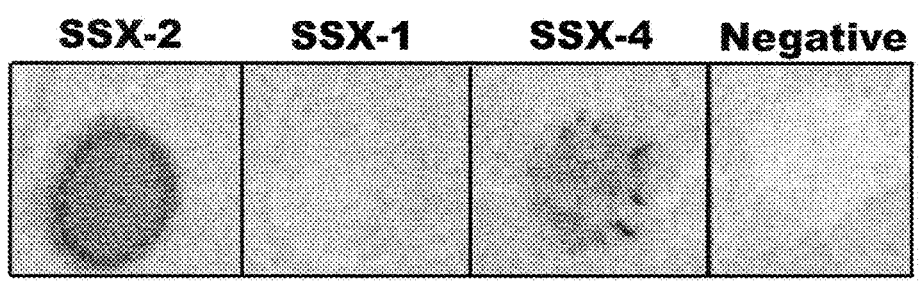
FIG. 1 shows an immunoblot (probed with anti-SSX-2/4 specific antibody) that confirmed protein expression. Phage encoding SSX-2, SSX-1, SSX-4 and a negative control (empty phage construct) were spotted directly onto a bacterial lawn. Proteins were transferred to an isopropyl-beta-D-thiogalactopyranoside (IPTG)-infused nitrocellulose membrane, and mouse anti-SSX-2 mAb (clone E3AS, with known reactivity to SSX-2 and SSX-4, but not SSX-1) was used to probe the membrane.

The present invention is based on the inventors' identification of a number of antigens to which patients with prostate cancer or melanoma have developed antibody immune responses. The prostate cancer antigens identified include SSX-2, MAD-Pro-30, MAD-Pro-42, transgelin, ZCWCC3, ACAA1, actinin and NFX2; whereas the melanoma antigens identified include MAD-CT-2, MAD-CT-1 and PAGE-1. The inventors have also found that prostate cancer cells as well as metastatic tissues express several of the above newly identified prostate cancer antigens (e.g., SSX-2). In addition, melanoma cells express several of the newly identified melanoma antigens (e.g., MAD-CT-2). The identification provides new tools for assisting the diagnosis and the detection of recurrence of prostate cancer and melanoma, especially for men. The identification also provides new tools for determining whether an immune therapy elicited a tumor-specific immune response.

The cancer antigens disclosed herein are known proteins, and their DNA and amino acid sequences are available in the art (see, e.g., Table 1). While it is envisioned that a prostate cancer or melanoma antigen identified by the inventors can be used by itself for the screening of prostate cancer and melanoma, respectively, a panel of more than one antigen is preferred. Other prostate cancer and melanoma antigens known in the art can be included in the panel. For example, a prostate cancer antigen panel may include SSX-2, NY-ESO-1, NFX2, MAD-Pro-22, MAD-Pro-30, MAD-Pro-34, MAD-Pro-42, MAD-CaP-1, MAD-CaP-5, MAD-CaP-15, MAD-CaP-20, MAD-CT-1, MAD-CT-2, MAD-CT-3, MAD-CT-5, transgelin, ZCWCC3, ACAA1, androgen receptor (AR; or ligand-binding domain of AR) and actinin. A smaller prostate cancer antigen panel may include SSX-2, NY-ESO-1, NFX2, MAD-Pro-22, MAD-Pro-30, MAD-Pro-34, MAD-Pro-42, MAD-CaP-1, MAD-CaP-5, MAD-CaP-15, MAD-CaP-20, MAD-CT-1, MAD-CT-2, MAD-CT-3, MAD-CT-5, transgelin, ZCWCC3, ACAA1 and AR (or ligand-binding domain of AR). Another smaller prostate cancer antigen panel may include SSX-2, NY-ESO-1, NFX2, MAD-Pro-22, MAD-Pro-30, MAD-Pro-34, MAD-Pro-42, MAD-CaP-1, MAD-CaP-5, MAD-CaP-15, MAD-CaP-20, MAD-CT-1, MAD-CT-2, MAD-CT-3, MAD-CT-5, transgelin, ACAA1 and AR (or ligand-binding domain of AR). Another smaller prostate cancer antigen panel may include MAD-Pro-34, MAD-Pro-42 and MAD-CT-2. Another smaller prostate cancer antigen panel may include SSX-2, MAD-Pro-30, AR (or ligand-binding domain of AR) and MAD-Pro-22 (PSA). Another smaller prostate cancer antigen panel may include MAD-Pro-30, AR (or ligand-binding domain of AR) and PSA.

An example of a melanoma antigen panel includes MAD-CT-2, SSX-2, NY-ESO-1, MAD-CT-1 and PAGE-1. A smaller melanoma antigen panel may include MAD-CT-2, SSX-2, NY-ESO-1 and PAGE-1. Another smaller melanoma antigen panel may include MAD-CT-2, SSX-2 and NY-ESO-1.

TABLE 1

Prostate and Melanoma cancer antigens.

| Designation Herein | Common Name | GenBank ID | SEQ ID NO: |
|---|---|---|---|
| MAD-Pro-22 | Prostate specific antigen (PSA) | NM_145864 | 57 |
| MAD-Pro-30 | Recombination signal binding protein (RBPJK) | NM_015874 | 58 |
| MAD-Pro-34 | Nucleolar autoantigen; SC6S; No55 | NM 006455.1 | — |
| MAD-Pro-42 | NY-CO-7/STUB1 | NM_005861 | 61 |
| MAD-CaP-1 | HMG17 | NM_005517 | — |
| MAD-CaP-5 | KIAA1404 gene product/ZNFX1 | NM_021035 | — |
| MAD-CaP-15 | CLL-associated antigen KW-12/RPL11 | NM_000975 | — |
| MAD-CaP-20 | Human bullous pemphigoid antigen | NM_015548 | — |
| MAD-CT-1 | Protamine 2 | NM_002762 | 68 |
| MAD-CT-2 | Hypothetical protein of unknown function FLJ40095/FLJ36144 | AK097414 | 67 |
| MAD-CT-3 | Sorting nexin 13 (SNX13) | NM_015132 | — |

TABLE 1-continued

Prostate and Melanoma cancer antigens.

| Designation Herein | Common Name | GenBank ID | SEQ ID NO: |
|---|---|---|---|
| MAD-CT-5 | Sjogren's syndrome antigen B (autoantigen La) | NM_003142 | — |
| SSX-2 | Synovial sarcoma, X breakpoint 2 | Z49105 | 60 |
| Transgelin | Transgelin | BC024296 | 62 |
| ZCWCC3 | Zinc-finger protein CW type with coiled domain 3 | NM_015358 | 63 |
| ACAA1 | Acetyl-coenzyme A acyltransferase 1 | NM_001607 | 64 |
| AR or AR-LBD | Androgen receptor (AR), or ligand-binding domain of AR | M20132 | 59 |
| Actinin | Actinin alpha 1, 2, 4 | D89980 | 65 |
| NY-ESO-1 | NY-ESO-1/CTAG1B | NM_001327 | 70 |
| PAGE-1 | PAGE1 | AF058989 | 69 |
| NFX2 | NFX2 | AF332009 | 66 |
| LAGE-1 | LAGE-1 | AJ223093 | — |

In one aspect, the present invention relates to a method for identifying a human subject as a candidate for further prostate cancer examination. The method includes the step of determining whether the human subject has developed an immune reaction to a prostate cancer antigen selected from SSX-2, MAD-Pro-30, MAD-Pro-42, transgelin, ZCWCC3, ACAA1, actinin and NFX2, wherein the presence of an immune reaction indicates that the human subject is a candidate for further prostate cancer examination. In one embodiment, a prostate cancer antigen panel as disclosed herein is used in the method and whether the human subject has developed an immune reaction to the antigens in the panel is determined. The presence of an immune reaction to any member of the panel indicates that the human subject is a candidate for further prostate cancer examination. For a subject who has already been indicated to have prostate cancer by other tests, the method here can be used to confirm the diagnosis or identify recurrence after treatment.

The method disclosed above may optionally include the step of subjecting a human subject to further prostate cancer examination if the human subject tests positive for at least one of the prostate cancer antigens. Any known test for assisting the diagnosis of prostate cancer can be used. Examples include serum prostate-specific antigen (PSA) blood test and standard pathological evaluation of prostate tissue specimen obtained from a biopsy. For subjects with a history of treated prostate cancer, radiographic scans can be conducted for detecting recurrent prostate cancer. In one embodiment, prostate or a prostate tissue specimen from the subject is examined for the presence of prostate cancer.

In a second aspect, the present invention relates to a method for determining whether an immune therapy elicited a tumor-specific immune response in a prostate cancer patient. In one embodiment, the immune therapy is an antigen-specific immune therapy. The new prostate cancer antigens identified herein can serve as targets for antigen-specific immune therapies and whether such an antigen-specific immune therapy has elicited a tumor-specific immune response can be determined by testing whether a patient has developed an immune reaction to the antigen. An antigen-specific immune therapy may ultimately elicit responses to other antigens (i.e., antigens other than the one the therapy is designed to specifically target). For example, a successful antigen-specific immune therapy causes immune-mediated tumor destruction, leading to recognition of other antigens. Therefore, response to another antigen (other than the one the therapy is designed to specifically target) in an antigen-specific immune therapy indicates indirectly that the therapy elicited an immune response to the targeted antigen and is therefore effective. To practice the method, the prostate cancer antigens disclosed herein can be used individually, in combination with each other, or in combination with other known prostate cancer antigens to determine whether an antigen-specific immune therapy has elicited a tumor-specific immune response. In this regard, whether the patient has developed an immune reaction to a prostate cancer antigen selected from SSX-2, MAD-Pro-30, MAD-Pro-42, transgelin, ZCWCC3, ACAA 1, actinin and NFX2 can be analyzed, wherein the presence of an immune reaction indicates that the therapy elicited a tumor-specific immune response. Any panel of prostate cancer antigens disclosed herein can be used for this purpose, wherein the presence of an immune reaction to at least one member of the panel indicates that the therapy elicited an immune response. Preferably, the patient is also tested for immune responses to the antigen or antigens before therapy so that it can be confirmed that an immune response detected after the start of the therapy is elicited by the therapy. The method may optionally include the step of monitoring the status of the prostate cancer in the patient by, e.g., the prostate cancer examination techniques described above.

In another embodiment of the second aspect, the immune therapy is a non-antigen-specific immune therapy. As used herein, "non-antigen-specific immune therapy" means an immune therapy that does not specifically target a particular antigen or an immune therapy that does not identify the antigen targets. Examples of non-antigen-specific therapies include whole-cell-based therapies such as the GVAX vaccines (granulocyte macrophage colony-stimulating factor-secreting cancer cell immunotherapy) or whole-cell vaccines developed by Onyvax Ltd. (London, England) (Hege K, et al., Int. Rev. Immunol. 25:321-352 (2006); Nemunaitis J, et al., Cancer Gene Ther. 13:555-562 (2006); and Michael A, et al., Clin. Cancer Res. 11:4469-4478 (2005)), cytokine-based therapies such as interleukin-2 or interferon-gamma (King D, et al. J. Clin. Oncol. 22:4463-4473 (2004)) or other immunomodulatory therapies including anti-CTLA-4 therapies used either alone or in combination with another therapy (Thompson R, et al., Urol. Oncol. 24:442-427 (2006); Korman A, et al., Adv. Immunol. 90:297-339 (2006); and Maker A, et al., Ann. Surg. Oncol. 12:1005-1016 (2005)). Traditionally, it has been difficult to assess whether a non-antigen-specific immune therapy generated a tumor-specific immune response because the therapy does not specifically target a particular antigen or the identities of the antigen targets are unknown. The prostate cancer antigens disclosed herein can be used individually, in combination with each other, or in combination with other known prostate cancer antigens to determine whether a non-antigen-specific immune therapy has elicited a tumor-specific immune response. In this regard, whether the patient has developed an immune reaction to a prostate cancer antigen selected from SSX-2, MAD-Pro-30, MAD-Pro-42, transgelin, ZCWCC3, ACAA1, actinin and NFX2 can be analyzed, wherein the presence of an immune reaction indicates that the therapy elicited a tumor-specific immune response. Any panel of prostate cancer antigens disclosed here can be used for this purpose, wherein the presence of an immune reaction to at least one member of the panel indicates that the therapy elicited an immune response. Preferably, the patient is also tested for immune responses to the antigen or antigens before therapy to confirm that an immune response detected after the start of the therapy is elicited by the therapy. The method may optionally include the step of monitoring the status of the prostate cancer in the patient by, e.g., the prostate cancer examination techniques described above.

In one embodiment, the method is used in clinical trials of antigen-specific or non-antigen-specific immune therapies for determining whether the therapies elicited a tumor-specific immune response.

One of ordinary skill in the art is more than capable of determining whether a human subject developed an immune reaction to one of the prostate cancer antigens. One way is to determine whether the human subject has produced antibodies to the antigens. For example, one can take a blood sample or blood-derived sample (e.g., a serum sample, a plasma sample or any preparation thereof that preserves the activity of immunoglobulins) from the human subject and test whether it contains antibodies to the antigens. Examples of such tests include enzyme-linked immunosorbent assay (ELISA), Western blot, protein microarray or high-throughput immunoblot analysis (Sreekumar A, et al., J. Natl. Cancer Inst. 96:834-843 (2004)), phage array-type analysis (Wang et al., supra; and Dubovsky J, et al., J. Immunother. 30:675-683 (2007)), and other methods known in the art. Another way is to determine whether the human subject has developed antigen-specific T cells, which is also well-known to one of ordinary skill in the art. For example, antigen stimulation can be used to detect antigen-specific T cells for their ability to proliferate, secrete various cytokines or exhibit cytolytic function (see e.g., Olson B & McNeel D, Prostate 67:1729-1739 (2007)). Other examples include enzyme-linked immunosorbent spot (ELISPOT) assays, fluorescence cell sorting of cytokine-producing cells, and peptide MHC/HLA tetramer assays (see e.g., Hobeika A, et al., J. Immunother. 28:63-72 (2005)). Preferably, circulating antigen-specific T cells are detected as they are the most accessible ones. For example, peripheral blood mononuclear cells (PBMC) can be analyzed for this purpose.

In a third aspect, the present invention relates to a method for identifying a human subject as a candidate for further melanoma examination. The method includes the step of determining whether the human subject has developed an immune reaction to a melanoma antigen selected from MAD-CT-2, MAD-CT-1 and PAGE-1, wherein the presence of an immune reaction indicates that the human subject is a candidate for further melanoma examination. MAD-CT-2 is a preferred melanoma antigen. In one embodiment, a melanoma antigen panel disclosed herein is used in the method and whether the human subject has developed an immune reaction to the antigens in the panel is determined. The presence of an immune reaction to any member of the panel indicates that the human subject is a candidate for further melanoma examination. For a subject already known to have melanoma by other tests, the method can be used to confirm the diagnosis or suggest recurrent disease.

The method disclosed above may optionally include the step of subjecting a human subject to further melanoma examination if the human subject is tested positive for at least one of the melanoma antigens. Any known test for assisting the diagnosing of melanoma can be used. For example, a skin specimen from the subject can be examined for the presence of melanoma (e.g., by pathological analysis). Radiographic imaging studies may be employed to evaluate for the presence of metastatic lesions.

In a fourth aspect, the present invention relates to a method for determining whether an immune therapy elicited a tumor-specific immune response in a melanoma patient. The method is the same as that described above for prostate cancer except that it is practiced with melanoma patients and the melanoma antigens identified by the inventors. In one embodiment, the immune therapy is an antigen-specific immune therapy. In another embodiment, the immune therapy is a non-antigen-specific immune therapy. The melanoma antigens disclosed here can be used individually, in combination with each other, or in combination with other known melanoma antigens to determine whether an immune therapy has elicited a tumor-specific immune response. In this regard, whether the patient has developed an immune reaction to a melanoma antigen selected from MAD-CT-2, MAD-CT-1 and PAGE-1 can be analyzed, wherein the presence of an immune reaction indicates that the therapy has elicited a tumor-specific immune response. Any panel of melanoma antigens disclosed herein can be used for this purpose, wherein the presence of an immune reaction to at least one member of the panel indicates that the therapy has elicited an immune response. Preferably, the patient is also tested for immune responses to the antigen or antigens before therapy so that it can be confirmed that an immune response detected after the start of the therapy is elicited by the therapy. The method may optionally include the step of monitoring the status of melanoma in the patient by, e.g., the melanoma examination techniques described above. In one application, the method is used in clinical trials of antigen-specific or non-antigen-specific immune therapies for determining whether the therapies have elicited a tumor-specific immune response.

Similar to what has been discussed above with respect to the prostate cancer antigens, it is well within the capability of one of ordinary skill in the art to determine whether a human subject has developed an immune reaction to one of the melanoma antigens, and examples of applicable techniques have been described above in connection with the prostate cancer antigens.

In a fifth aspect, the present invention relates to yet another method for identifying a human subject as a candidate for further melanoma examination. The method includes the step of determining whether the cells in a region of the subject's skin suspected of being malignant express MAD-CT-2, wherein the expression of MAD-CT-2 indicates that the subject is a candidate for further melanoma examination. The expression of MAD-CT-2 can be determined at either the mRNA level or the protein level and one of ordinary skill in the art is familiar with the techniques for such determination. For example, antibodies directed to an epitope on an antigen can be used to detect the antigen at the protein level, and it is well within the capability of one of ordinary skill in the art to generate such antibodies if not already available. The presence of mRNA for an antigen can be measured using methods for hybridizing nucleic acids, including, without limitation, RNA, DNA and cDNA. Such methods are generally known to those skilled in the art (e.g., RT-PCR amplification, Northern blot and Southern blot).

Optionally, the method further includes the step of subjecting a human subject who is positive for the expression of MAD-CT-2 to further melanoma examination. For a subject already identified as having melanoma by other tests, the method provided herein can be used to confirm the diagnosis.

In sixth aspect, the present invention relates a method for identifying candidate compounds for further testing as preventive or therapeutic agents for melanoma. As MAD-CT-2 is expressed in melanoma cells, it can serve as a marker for melanoma drug screening because, presumably, an anti-melanoma agent can bring down the MAD-CT-2 mRNA and protein level in melanoma cells that express this marker. Accordingly, a compound that demonstrates such an activity may be a good candidate for further testing for anti-tumor efficacy. In this regard, animal or human cells that express MAD-CT-2 can be exposed to a test agent, and the effect of the test agent on MAD-CT-2 expression at the mRNA or protein level relative to that of corresponding untreated control cells can be measured, wherein a lower expression than that of the control cells indicates that the agent is a candidate for further testing as preventive or therapeutic agents for melanoma. The animal or human cells that express MAD-CT-2 can contain a DNA sequence encoding MAD-CT-2 under the control of an endogenous promoter such as a native promoter or another promoter following translocation to a new site. Preferably, human or animal melanoma cells that express MAD-CT-2 are used. In one embodiment, such human or animal melanoma cells are those of a cell line.

In seventh aspect, the invention relates to kits suitable for use in the methods disclosed herein. For the method of identifying a human subject as a candidate for further prostate cancer examination in connection with analyzing whether the subject has developed an immune response to prostate cancer antigens, the kit includes the proteins or suitable fragments thereof of a prostate cancer antigen panel disclosed herein or expression vectors/systems for expressing the proteins or suitable fragments (e.g., a phage system as described in Example 1 below, an expression vector containing a DNA sequence encoding an antigen protein operably linked to a promoter such as a non-native promoter, or a cell containing the expression vector). In this regard, a protein in the panel can be represented by the protein with additional amino acid sequences at one or both of the N- and C-terminal ends, as long as the additional sequences do not affect the function of the proteins in connection with the present invention (i.e., the ability to bind to the corresponding immunoglobulins). The additional amino acid sequences can, but do not have to, assist in the purification, detection, or stabilization of the proteins. Optionally, the kit also includes a positive control, a negative control or both. For example, a positive control may be a composition containing an antibody to one or more of the antigens in the panel (e.g., a blood/serum/plasma preparation from a patient or group of patients known to interact with one or more of the antigens). A negative control for the proteins in the panel and the expression vectors/systems for expressing the proteins may be a non-tumor antigen protein such as a housekeeping protein and an expression vector/system for expressing the non-tumor antigen. A negative control for the patient's serum or blood-derived sample may be a serum or blood-derived sample from a normal individual that does not interact with any of the proteins in the panel.

For the method of identifying a human subject as a candidate for further melanoma examination in connection with analyzing whether the subject developed an immune response to melanoma antigens, the kit includes the proteins or suitable fragments thereof of a melanoma antigen panel disclosed herein or expression vectors/systems for expressing the proteins or suitable fragments (e.g., a phage system as described in Example 1 below, an expression vector containing a DNA sequence encoding an antigen protein operably linked to a promoter such as a non-native promoter, or a cell containing the expression vector). In this regard, a protein in the panel can be represented by the protein with additional amino acid sequences at one or both of the N- and C-terminal ends, as long as the additional sequences do not affect the function of the proteins in connection with the present invention (i.e., the ability to bind to the corresponding immunoglobulins). The additional amino acid sequences can, but do not have to, assist in the purification, detection or stabilization of the proteins. Optionally, the kit also includes a positive control, a negative control or both. For example, a positive control may be a composition containing an antibody to one or more of the antigens in the panel (e.g., a blood/serum/plasma preparation from a patient known to interact with one or more of the antigens). A negative control for the proteins in the panel and the expression vectors/systems for expressing the proteins may be a non-tumor antigen protein, such as a housekeeping protein and an expression vector/system for expressing the non-tumor antigen. A negative control for the patient's serum or blood-derived sample may be a serum or blood-derived sample from a normal individual that does not interact with any of the proteins in the panel.

For the method of identifying a human subject as a candidate for further melanoma examination in connection with analyzing the expression of MAD-CT-2, the kit includes an antibody to MAD-CT-2 or an oligonucleotide set for amplifying and detecting MAD-CT-2 mRNA or cDNA. For example, the oligonucleotide set can contain a pair of PCR primers, preferably RT-PCR primers, which can be used for both amplifying and detecting the mRNA or cDNA. The set may also contain a separate oligonucleotide for detecting the amplified sequence. Optionally, the kit also includes a positive control, a negative control or both. For example, a positive control may be a composition that contains MAD-CT-2 or the corresponding mRNA or cDNA (e.g., melanoma cells or an extract thereof of either a cell line or a patient that are known to express MAD-CT-2). A negative control for the cells from a subject being tested may be cells that do not express MAD-CT-2 (e.g., skin cells or other types of cells from a normal individual). A negative control for the antibody or oligonucleotide set may be an antibody that does not interact with MAD-CT-2 or a set of oligonucleotides that does not amplify and detect the corresponding mRNA/cDNA (e.g., an antibody to a non-tumor antigen protein, such as a housekeeping protein or a set of oligonucleotides that amplifies and detects the mRNA/cDNA of the non-tumor antigen protein).

Any of the kits described above can optionally contain an instruction manual directing use of the kit according to the method of the present invention.

The invention will be more fully understood upon consideration of the following non-limiting examples.

EXAMPLES

Example 1

Antibody Responses to Cancer-Testis Antigens in Melanoma Patients

In this example, we show the construction of a panel of 29 CTA in lambda (λ) phage, and implementation of a novel high throughput immunoscreening method using a panel of sera from patients with melanoma (n=44) and volunteer blood donors (n=50). We show that antibody responses occurred in 39% of patients with melanoma to at least one CTA antigen in a defined panel of 5 compared with 4% of controls (p<0.001). Moreover, antibody responses to one antigen, MAD-CT-2, occurred in 27% of patients compared with 0/50 controls (p<0.0001). We also show that MAD-CT-2 is expressed in melanoma cell lines.

Materials and Methods.

Subject Population: Sera were obtained from 44 male patients with metastatic melanoma, mean age 50 years (range 25-78 years). All patients had been treated with primary resection. 19/44 (43%) were treated with prior immunotherapy, and 9/44 (20%) were treated with prior chemotherapy. All subjects gave written institutional review board (IRB)-approved informed consent for their blood products to be used for immunological research. Blood was collected at the University of Wisconsin Hospital and Clinics (Madison, Wis.), and sera were stored in aliquots at −80° C. until used. Control sera were obtained from volunteer male blood donors, mean age 34 years (range 18-57 years), who also gave IRB-approved written informed consent.

Phage Cloning: Plasmid DNA encoding full-length cDNAs for 29 CTA were either purchased as IMAGE clones (American Type Culture Collection (ATCC); Manassas, Va.), or were obtained from cDNA expression libraries from previous studies (Hoeppner et al., supra; and Stone B, et al., Int. J. Cancer 104:73-84 (2003)). Primers, specific for each CTA, were designed with the purpose of appending a single 5' EcoRI and a single 3' XhoI site for subcloning. In cases where the CTA had an internal EcoRI or XhoI site, an alternate 5' MfeI site or 3' SalI site was used. Table 2 shows the sequence of the primers and IMAGE clone identification for each CTA construct. Polymerase chain reaction (PCR) was performed using template cDNAs, gene specific primers, Taq polymerase (Promega; Madison, Wis.), and 30 amplification cycles optimized with respect to temperature for each primer pair. PCR products were gel purified (Qiaquick Gel Extraction Kit; Qiagen; Valencia, Calif.), digested with the appropriate restriction enzymes, and ligated into λ-phage arms (Lambda ZAP express protocol; Stratagene; La Jolla, Calif.). Phage were amplified by standard methods and sequenced to confirm their identity and to detect any mutations introduced by PCR (Table 2).

TABLE 2

CTA phage construction. Shown are the names and GenBank identifiers for each CTA chosen for analysis. In addition, the 5' and 3' primers used for the gene-specific cDNA PCR amplification and subcloning are shown, and the IMAGE clone identifiers from which the genes were cloned. Variations from the published amino acid sequences identified after final clone sequencing are shown.

| Name | GenBank ID | Image Clone ID | 5' Primer | 3' Primer | Sequence variation: |
|---|---|---|---|---|---|
| MAGE-A1[1] | NM_004988 | | GGAATTCATGTCTCTTGAGCAGAGGAGTC (SEQ ID NO:1) | CCGCTCGAGCTCAGACTCCCTCTTCCTCCTC (SEQ ID NO:2) | |
| SSX2[2] | BC007343 | | GGTGCTCAAATACCAGAGAAG (SEQ ID NO:3) | CTTTGGGTCCAGATCTCTCGTG* (SEQ ID NO:4) | |

TABLE 2-continued

CTA phage construction. Shown are the names and GenBank identifiers for each CTA chosen for analysis. In addition, the 5' and 3' primers used for the gene-specific cDNA PCR amplification and subcloning are shown, and the IMAGE clone identifiers from which the genes were cloned. Variations from the published amino acid sequences identified after final clone sequencing are shown.

| Name | GenBank ID | Image Clone ID | 5' Primer | 3' Primer | Sequence variation: |
|---|---|---|---|---|---|
| NY-ESO-1[3] | AJ003149 | | GGAATTCCATGCAGGCCGAAGGCCGGGG (SEQ ID NO:5) | CCGCTCGAGCTTAGCGCCTCTGCCCTGAGGG (SEQ ID NO:6) | G to V mutation at a.a.#41 |
| GAGE-7[4] | NM_021123 | | GGAATTCATGAGTTGGCGAGGAAGATCGACC (SEQ ID NO:7) | CCGCTCGAGTTAACACTGTGAGCTTTTCACC (SEQ ID NO:8) | |
| SSX4[5] | U90841 | | GGAATTCATGAACGGAGACGACGCCTTG (SEQ ID NO:9) | CCGCTCGAGTTACTCGTCATCTTCCTCAGGG (SEQ ID NO:10) | |
| NXP2[6] | BC015020 | 3921074 | CCAATTGATGTGCTCTACTCTAAAGAAGTGTG (SEQ ID NO:11) | CCGCTCGAGTTAGGAGATTTGCTTGAAGGCCTCTG (SEQ ID NO: 12) | |
| TPX1[7] | BC022011 | 4826427 | GGAATTCAATGGCTTTACTACCGGTGTTGTTTC (SEQ ID NO:13) | CCGCTCGAGTCAGTAAATTTTGTTCTCACATAGG (SEQ ID NO:14) | |
| XAGE-1[8] | BC009538 | 3893227 | GGAATTCATGGAGAGCCCCAAAAAGAAGAACC (SEQ ID NO:15) | CCGCTCGAGTTAAACTTGTTGCTCTTCACCTG (SEQ ID NO:16) | |
| LAGE-1[9] | BC002833 | 3638129 | GGAATTCATGCAGGCCGAAGGCGGGGCAC (SEQ ID NO:17) | CCGCTCGAGCTAAATGAGAGGGGCAGAGAACATC (SEQ ID NO:18) | |
| PAGE-1[4] | BC010897 | 4043535 | GGAATTCGATGAGTGCACGAGTGAGATCAAG (SEQ ID NO:19) | CCGCTCGAGTTATGGCTGCCCATCCCTGCTTC (SEQ ID NO:20) | |
| MAGE-E1[10] | BC081566 | 6292139 | CCAATTGCATGGCTGAGGGAAGCTTCAGCGTG (SEQ ID NO:21) | CCGCTCGAGTCAACGGTGCTGGATCCAGGAG (SEQ ID NO:22) | |
| SPANXC[11] | BC054023 | 6648369 | CCAATTGATGGACAAACAATCCAGTGCCGGCGG (SEQ ID NO:23) | CCGCTCGAGCTACTTTGCAGGTATTTCACATTATTTC (SEQ ID NO:24) | Missing last 7 a.a.'s |
| ADAM2[12] | BC064547 | 5744846 | GGAATTCATGTGGCGCGTCTTGTTTCTGCTC (SEQ ID NO:25) | CGGCTCGAGACTACCCTTTAGGTTCACTCTCAC (SEQ ID NO:26) | |
| TSP50[13] | BC037775 | 5272458 | GGAATTCATGGGTCGCTGGTGCCAGACCGTC (SEQ ID NO:27) | CCGCTCGAGTCAGAGGGCAGCAAGGAGG (SEQ ID NO:28) | |
| NY-SAR-35[14] | BC034320 | 4836772 | GGAATTCATGTCTTCACATAGGAGGAAAGGGAAG (SEQ ID NO:29) | CCGCTCGAGCTACTCGTCACCATGTTCCTCAC (SEQ ID NO:30) | |
| FATE1[15] | BC022064 | 4826440 | GGAATTCATGGCAGGAGGCCCTCCCAACACC (SEQ ID NO:31) | CCGCTCGAGATCACTGGTTCATCCACAGCCAC (SEQ ID NO:32) | |
| PAGE-5[12] | BC009230 | 3955765 | GGAATTCGTGATGCAGGCGCCATGGGCC (SEQ ID NO:33) | CCGCTCGAGCTATAGTTGCCCTTCACCTGCTTGG (SEQ ID NO:34) | |
| LIP1[12] | BC023635 | 4841470 | GGAATTCATGTCTCTACGCTGCGGGGATGCAG (SEQ ID NO:35) | CCGCTCGAGTTTAGAGGTCTTTTGTTTTTCTTTTAGCC (SEQ ID NO:36) | |
| SPA17[16] | BC032457 | 5171849 | CCAATTGATGTCGATTCCATTCTCCAACACC (SEQ ID NO:37) | CCGCTCGAGTCACTTGTTTTCCTCTTTTTCCTC (SEQ ID NO:38) | |

TABLE 2-continued

CTA phage construction. Shown are the names and GenBank identifiers for each
CTA chosen for analysis. In addition, the 5' and 3' primers used for the
gene-specific cDNA PCR amplification and subcloning are shown, and the IMAGE
clone identifiers from which the genes were cloned. Variations from the
published amino acid sequences identified after final clone sequencing are shown.

| Name | GenBank ID | Image Clone ID | 5' Primer | 3' Primer | Sequence variation: |
|---|---|---|---|---|---|
| MAGE-A8[1] | BE387798 | | GGAATTCATGCCTCTTGAGCAGAGGAGTCAG (SEQ ID NO:39) | CCGCTCGAGACTCACTCTTCCCCCTCTCTCAA (SEQ ID NO:40) | |
| MAGE-B1[17] | BE897525 | | GGAATTCATGCCTCGGGGTCAGAAGAG (SEQ ID NO:41) | ACGCGTCGACTCACATGGGGTGGGAGGACCTG (SEQ ID NO:42) | |
| MAGE-B2[17] | BC026071 | | GGAATTCATGCCTCGTGGTCAGAAGAGTAAG (SEQ ID ND:43) | CCGCTCGAGCTCAGACTCCGGCTTTCTCTTC (SEQ ID NO:44) | |
| MAGE-A4[1] | BC017723 | | GGAATTCATGTCTTCTGAGCAGAAGAGTC (SEQ ID NO:45) | CCGCTCGAGCTCAGACTCCCTCTTCCTCCT (SEQ ID NO:46) | |
| SSX1[2] | BC01003 | 3445470 | GGAATTCATGAACGGAGACAACACCTTTG (SEQ ID NO:47) | CCGCTCGAGTTACTCGTCATCTTCCTCAGGG (SEQ ID NO:48) | |
| GAGE-2[12] | BC069397 | 7262151 | GGAATTCATGAGTTGGCGAGGAAGATCGACC (SEQ ID NO:49) | CCGCTCGAGTTAACACTGTGATTGCTTTTCACCTTC (SEQ ID NO:50) | |
| GAGE-4[16] | BC069470 | | GGAATTCATGATTGGGCCTATGCGGCCCGAG (SEQ ID NO:51) | CCGCTCGAGTTAACACTGTGATTGCCCTTCACCTTC (SEQ ID NO:52) | |
| MAGE-A3[1] | BC016803 | | * | * | |
| MAD-CT-1[19] | NM_002762 | | GAGGAGCCTGAGCGAACG* (SEQ ID NO:53) | GGAATTCTTAGTGCCTTCTGCATGTTCTCTT* (SEQ ID NO:54) | |
| MAD-CT-2[18] | AK097114 | | GAGGATATGAGATCAGAAAGAGAAG* (SEQ ID NO:55) | TCCACACTGCCAGTGTGGCTCAT* (SEQ ID NO:56) | |

*Phage encoding MAGE-A3 were obtained from previous unpublished studies.
[1]De Plaen E et al. Immunogenetics 1994, 40:360-369.
[2]Crew AJ et al. Embo J. 1995, 14:2333-2340.
[3]Chen YT et al. Proc. Natl. Acad. Sci. U.S.A. 1997, 94:1914-1918.
[4]Chen ME et al. J Biol Chem. 1998,273:17618-17625.
[5]Gure AO et al. Int J Cancer 1997, 72:965-971.
[6]Loriot A et al. Int J Cancer 2003, 105:371-376.
[7]Kasahara M et al. Immunogenetics 1989, 29:61-63.
[8]Brinkmann U et al. Cancer Res. 1999, 59:1445-1448.
[9]Chen YT et al. Proc Natl Acad Sci U.S.A. 1998, 95:6919-6923.
[10]Sasaki M et al. Cancer Res. 2001,61:4809-4814.
[11]Zendman AJ et al. Cancer Res. 1999, 59:6223-6229.
[12]Scanlan MJ et al. Int J Cancer 2002, 98:485-492.
[13]Yuan L et al. Cancer Res. 1999, 59:3215-3221.
[14]Lee SY et al. Proc Natl Acad Sci U.S.A. 2003, 100:2651-2656.
[15]Dong XY et al. Br J Cancer 2003, 89:291-297.
[16]Lim SH et al. Blood 2001, 97:1508-1510.
[17]Lurquin G et al. Genomics 1997, 46:397-408.
[18]Van den Eynde B et al. J Exp Med. 1995, 182:689-698
[19]Hoeppner LH et al. Cancer Immun. 2006, 6:1-7.

Reverse transcriptase-PCR (RT-PCR): E. coli cultures (XL-1 blue MRF strain; Stratagene) were transduced with $10^6$ pfu of individual phage and grown overnight in LB media+20 mM $MgSO_4$+0.2% maltose+2.5 mM isopropyl-beta-D-thiogalactopyranoside (IPTG) at 37° C. Total RNA was prepared from centrifugally pelleted cultures (RNeasy Mini Columns; Qiagen). RT-PCR reactions were conducted using the Qiagen One-Step RT-PCR Kit (Qiagen) and transcript-specific primers (T7 Promoter and T3 Promoter; Invitrogen; Carlsbad, Calif.). To control for the possible amplification of contaminating genomic or phage DNA in the total RNA preparations, duplicate reactions were first heated to 100° C. for 10 minutes immediately prior to the normal RT-PCR reaction to attenuate reverse transcriptase activity. PCR amplification reactions were resolved on agarose gels and the size of the amplified transcript confirmed by comparison with DNA size markers (1 Kb ladder; Promega).

High Throughput Immunoblot: XL-1 blue MRF E. coli were grown overnight at 31° C. in LB medium supplemented with 20 mM $MgSO_4$ and 0.2% maltose. Cultured cells were then collected by centrifugation, resuspended in 10 mM $MgSO_4$, and poured in top agarose (LB broth/10 mM $MgSO_4$/0.2% maltose/0.7% agarose) over LB agar in Omniwell plates (Nunc). 9,000 pfu of individual phage were then spotted in a 0.9 µl volume in replicates onto multiple bacterial agar lawns using a liquid handling robot (Beckman; Biomek FX; Fullerton, Calif.). Spotted plates were allowed to sit undisturbed for 15 minutes at room temperature, and then overlaid with nitrocellulose membranes impregnated with 10 mM IPTG. Plates were incubated overnight at 37° C. The next day, filters were gently peeled from bacterial lawns and washed twice in TBST (50 mM Tris pH 7.2, 100 mM NaCl, 0.5% Tween-20) for 5 minutes and once in TBS (50 mM Tris pH 7.2, 100 mM NaCl) for an additional 5 minutes. The filters were then blocked in TBS+1% BSA for 1 hour shaking at room temperature.

Membranes were then probed with human serum preabsorbed to E. coli proteins and the empty phage construct diluted 1:100 in blocking solution at 4° C. overnight. Following this, the membranes were again washed twice in TBST and once in TBS, and human IgG was detected with anti-human IgG-AP (Sigma; St. Louis, Mo.) diluted 1:25,000 in blocking solution for 1 hour shaking at room temperature. The filters were again washed and then developed with 0.3 mg/ml nitro-blue tetrazolium chloride (NBT)+0.15 mg/ml 5-bromo-4-chloro-3'-indolyphosphate p-toluidine salt (BCIP). After development, filters were washed with deionized water, and then dried prior to evaluation. Immunoreactive plaques were recorded for each filter by visual comparison with an internal positive (phage encoding human IgG) and negative (empty phage encoding beta-galactosidase) control plaques. A plaque was defined as positive if replicate plaques were read as positive and there was accordance among at least six of nine independent observers, to reduce the possibility of subjective interpretation (Dunphy E, et al., J. Clin. Immunol. 24:492-501 (2004)). Comparison of immunoreactive spots among subject groups was made by chi-square analysis.

Western blot: Amino-terminal glutathione-S-transferase (GST) linked SSX-2 and GST (control) were purified from IPTG-induced overnight E. coli (Rosetta Gami expression strain) cultures transformed with pET41b plasmid (EMD Biosciences; San Diego, Calif.) containing full length SSX-2 cloned in frame with the ATG start codon. Purified proteins were stored at −80° C. and were thawed immediately before mixing 1:1 with 2× SDS Laemmli's loading buffer (0.04 M Tris pH 6.8, 12% glycerol, 1.25% sodium docecyl sulfate (SDS), 3% β-mercaptoethanol, 0.06% bromophenol blue) and boiling for 10 minutes at 100° C. The proteins were then resolved on 15% SDS-polyacrylamide gels and were electrophoretically transferred to nitrocellulose membranes. Membranes were then probed, using standard immunoblot techniques, with preabsorbed patient sera diluted 1:200 in blocking solution or protein-specific antibodies. Detection antibodies included goat anti-SSX-2 polyclonal antibody (N-16; Santa Cruz Biotechnology; Santa Cruz, Calif.), and anti-GST monoclonal antibody (rabbit A5800; Invitrogen; Carlsbad, Calif.).

Results.

Cloning and validation of λ phage encoding CTA: We wished to develop a tool permitting simultaneous analysis of antibody responses to multiple antigens within a single serum sample. Given the ease of λ phage cloning and expression compared with standard methods of protein purification, we chose to use a phage expression array methodology, similar to what we have previously described (Dunphy E J et al. J. Clin. Immunol. 2004, 24:492-501). Consequently, cDNA encoding 25 unique CTA were amplified by PCR, ligated into λ phage arms, packaged into phage particles, and sequenced to confirm their identity. In addition, phage encoding SSX-2, MAGE-A3, MAD-CT-1 and MAD-CT-2 were available from prior studies (Hoeppner et al., supra; Crew A, et al., Embo. J. 14:2333-2340 (1995); and De Plaen E, et al., Immunogenetics 40:360-369 (1994), each of which is incorporated herein by reference as if set forth in its entirety). Gene transcription from each CTA phage construct was evaluated using RT-PCR reactions on total RNA purified from phage-transduced E. coli. In all cases, CTA phage produced mRNA transcripts of the correct predicted size. Similarly, immunoblot confirmed protein expression of CTA for which antibody reagents were available. For example, FIG. 1 demonstrates that a monoclonal antibody recognizing SSX2 and SSX4 could identify protein expression from phage-transduced E. coli.

Antigen-specific IgG to a panel of CTA were detected by high throughput immunoblot (HTI): Phage encoding individual CTA were directly spotted onto bacterial lawns grown in top agarose using a Biomek FX liquid handling robot. Optimization studies showed that a volume of 0.9 µl of $10^4$ pfu/µl phage produced reproducibly dense plaques. After plating and transfer to nitrocellulose membranes, the filters were probed with human sera that had been preabsorbed for antibodies to E. coli and diluted 1:100. Specifically, sera were obtained from 44 male patients with metastatic melanoma, and 50 male controls without cancer, and used to probe 94 individual membranes. Human IgG was then detected and visualized as described. Within each spotted array, phage encoding human IgG were included as a positive control, and empty phage were included as a negative control. In our hands, by using the liquid handling robot to uniformly array phage, we could easily screen at least 100 sera at the same time and accomplish the entire screening in three days.

Given the presence of internal positive and negative control phage plaques on each membrane, several methods were initially evaluated to objectively evaluate the final immunoblot membranes in an automated fashion. These methods included using fluorescent analysis of membranes following the use of fluorescent-tagged secondary antibodies, and automated densitometric analysis following calorimetric staining (not shown). Unfortunately, given variable backgrounds due to the E. coli bacterial lawns, these methods were unreliable and frequently "missed" plaques that were clearly immunoreactive, and false positive plaques were often observed. Consequently, we found that visual inspection was more accurate. To eliminate subjectivity from this evaluation, and reduce the possibility of false positive interpretation, each filter was reviewed and scored by a panel of independent readers. Plaques were scored as immunoreactive if duplicate plaques were each scored positive by the same observer, and if there was concordance among at least 6 of 9 independent observers, similar to what we have previously reported (Dunphy E, et al., J. Clin. Immunol. 24:492-501 (2004)). A subset of sera was re-evaluated in similar fashion to confirm the reproducibility of the findings, and immunoreactive plaques were similar to those observed in the initial screening (data not shown).

Figure 2:
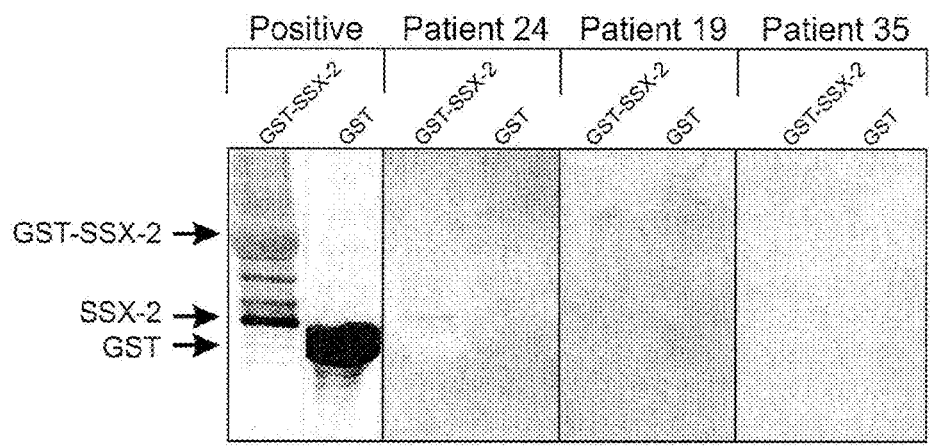
FIG. 2 shows that high throughput immunoblot (HTI) detected CTA-specific IgG in patient sera. A) Purified glutathione-S-transferase (GST)-SSX-2 and GST were evaluated by Western blot with patient sera (patients 24, 19 or 35) or with monoclonal antibodies (positive) specific for SSX-2 or GST. B) HTI conducted with CTA phage array using sera from patients 24, 19 or 35. Positive refers to phage encoding IgG, and negative refers to empty phage control.
Figure 2:
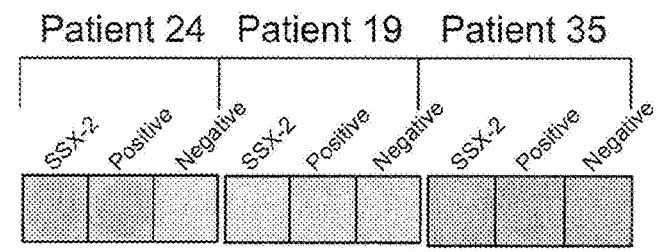

The presence of IgG specific for SSX-2 was confirmed by Western blot analysis: Western blot analysis was used when possible to confirm responses to CTA identified by HTI. As shown in FIG. 2A, IgG specific for SSX-2 were detectable by Western blot using sera from patient 24, a patient found by HTI to have IgG specific for SSX-2 (FIG. 2B). Conversely, no response was detectable using sera from patients 19 or 35 from whom no detectable HTI response to SSX-2 was detected, indicating that HTI screening provided data consistent with that by Western blot analysis.

Figure 3:
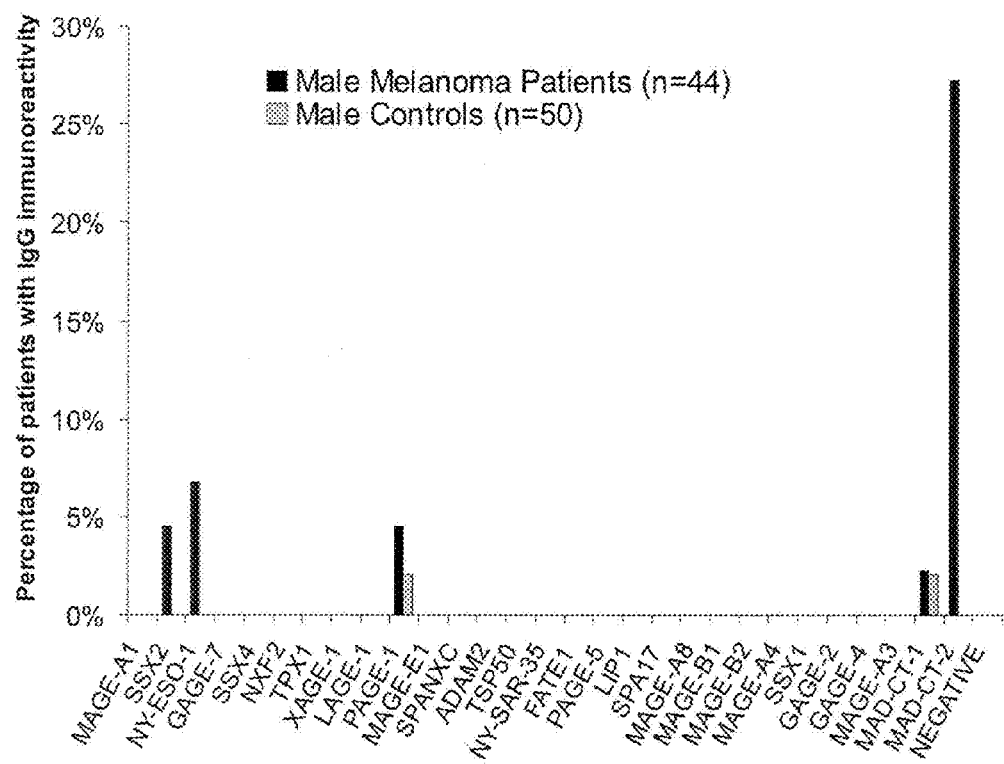
FIG. 3 shows that patients with melanoma have IgG specific for several CTA. Shown is the percentage of male patients with melanoma (n=44), or male control blood donors without cancer (n=50), with IgG specific for each of the 29 CTA tested.

Patients with melanoma have frequent antibody responses to SSX-2, NY-ESO-1, and MAD-CT-2: As shown in FIG. 3, IgG responses to SSX-2 and NY-ESO-1 were detected in 2/44

Figure 4:
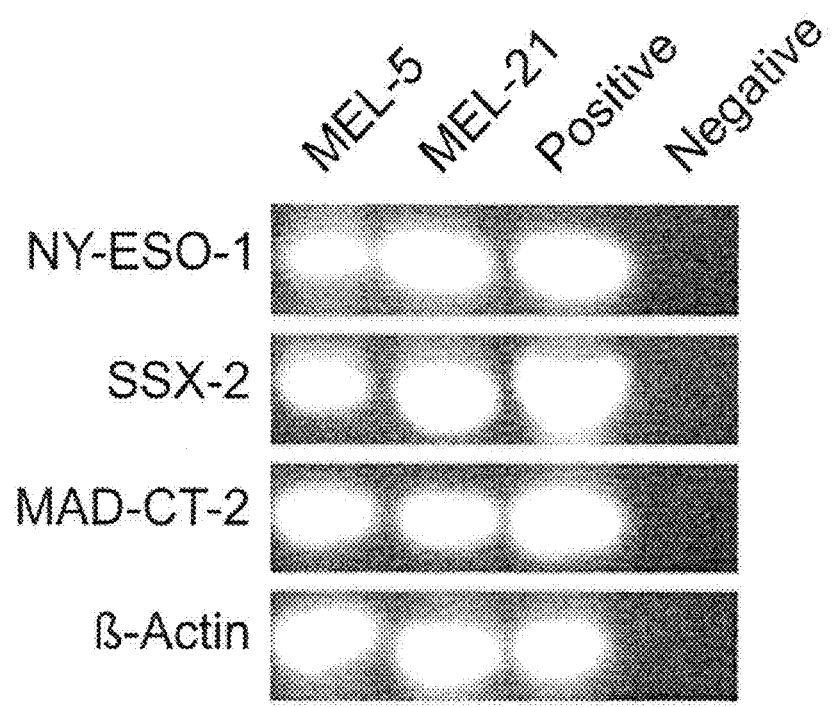
FIG. 4 shows that MAD-CT-2, NY-ESO-1 and SSX-2 are expressed in melanoma cell lines. RT-PCR (reverse transcriptase-polymerase chain reaction) with primers specific for NY-ESO-1, SSX-2, MAD-CT-2 or β-actin was conducted using mRNA from cell lines (e.g., MEL-5 and MEL-21), cDNA encoding each of the proteins (positive control), or no DNA template (negative control).

(5%, p=0.13) and 3/44 (7%, p=0.061) patients, respectively, compared with 0/50 male controls. In addition, IgG responses to MAD-CT-2 were identified in 12/44 (27%) of patients compared with 0/50 controls (p<0.001). IgG responses were also detected at lower frequencies to PAGE-1 and MAD-CT-1. Overall, IgG responses to at least one of the CTA were detected in 17/44 (39%) of male patients with melanoma, compared with 2/50 (4%) of controls (p<0.001) (FIG. 3 and Table 3). There was no apparent association with whether patients had been previously treated with immunotherapy, as 7/17 patients with antibody responses had been previously treated with immunotherapy (41%) compared with 12/27 patients who had no CTA-specific antibody responses (44%, p=0.83). IgG responses to MAD-CT-2 were detected in patients who did not demonstrate reactivity to SSX-2 or NY-ESO-1 (Table 3). This did not appear to be due to differences in patterns of gene expression, as mRNA encoding all three gene products were detectable in two different melanoma cell lines tested (FIG. 4). The identification of MAD-CT-2 transcripts in melanoma cell lines, however, demonstrates that it is a melanoma CTA.

TABLE 3

IgG responses to at least one CTA were detectable in multiple patients with melanoma. Shown are the patients with serum IgG specific for each CTA (shaded box) arrayed against the CTA tested.

| Patient # | SSX2 | NY-ESO-1 | PAGE-1 | MAD-CT-1 | MAD-CT-2 | Negative | Positive |
|---|---|---|---|---|---|---|---|
| 2 | | | | | | | ■ |
| 3 | | | | | | | ■ |
| 4 | | | | | | | ■ |
| 8 | | | | | | | ■ |
| 16 | | | | | | | ■ |
| 18 | | | | | | | ■ |
| 21 | | | | | ■ | | ■ |
| 22 | | | | | ■ | | ■ |
| 30 | | | | | ■ | | ■ |
| 32 | | | | | ■ | | ■ |
| 36 | | | | | ■ | | ■ |
| 39 | | | | | ■ | | ■ |
| 20 | | ■ | | | | | ■ |
| 24 | | ■ | | | | | ■ |
| 31 | | | ■ | | | | ■ |
| 33 | | | ■ | | | | ■ |
| 35 | | | ■ | | | | ■ |

Example 2

Antibody Responses to Cancer-Testis Antigens in Prostate Cancer Patients

Using techniques similar to those described in Example 1 above or an ELISA assay, the inventors have found that antibody responses occurred at a higher rate in prostate cancer patients than in control individuals for the following antigens: SSX-2, NY-ESO-1, LAGE-1, NFX2, MAD-Pro-22, MAD-Pro-30, MAD-Pro-34, MAD-Pro-42, MAD-CaP-1, MAD-CaP-5, MAD-CaP-15, MAD-CaP-20, MAD-CT-1, MAD-CT-2, MAD-CT-3, MAD-CT-5, transgelin, ZCWCC3, ACAA1, AR (or ligand-binding domain of AR) and actinin. The results are summarized in Table 4 with the results obtained by either ELISA assays (labeled) or using the techniques described in Example 1. The ELISA assays were conducted using purified antigen proteins which were probed with sera from prostate cancer patients or normal individuals followed by detection of antigen-antibody interaction using enzyme-conjugated anti-human Ig antibody and the corresponding enzyme substrate.

Figure 5:
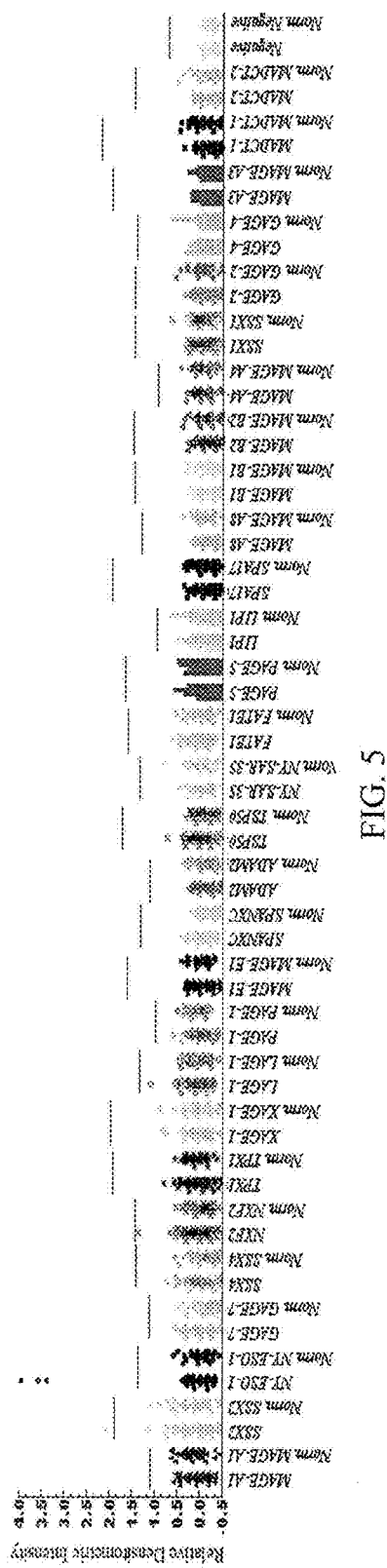
FIG. 5 shows that HTI identified IgG responses to 4 (i.e., SSX-2, NY-ESO-1, LAGE-1 and NFX2) of 29 known CTA using sera from prostate cancer patients.

FIG. 5 shows a specific example of the studies conducted with the techniques described in Example 1 in which SSX-2, NY-ESO-1, LAGE-1, and NFX2 were found to be expressed at a higher rate in prostate cancer patients than in control individuals.

Figure 6:
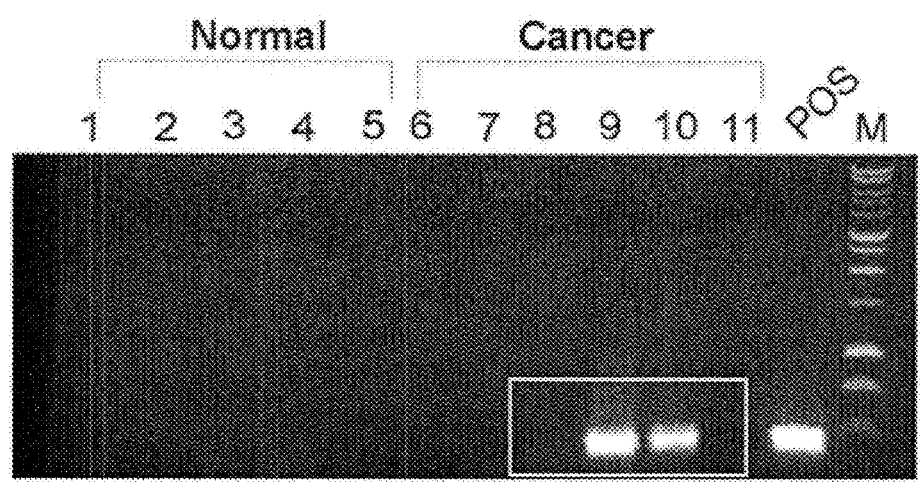
FIG. 6 shows the expression of SSX-2 in 5 normal prostate epithelial cell lines (lanes 1-5: 1. PrEC1; 2. PrEC2; 3. PrEC3; 4. PrEC4; and 5. PZ-HPV7) and 6 prostate cancer cell lines (lanes 6-11: 6. SWPC1; 7. SWPC2; 8. SWNPC2; 9. LAPC4; 10. MDAPCa2b; and 11. MDAPCa2a) by RT-PCR. POS represents a cDNA positive control; whereas M represents molecular weight markers.
Figure 7:
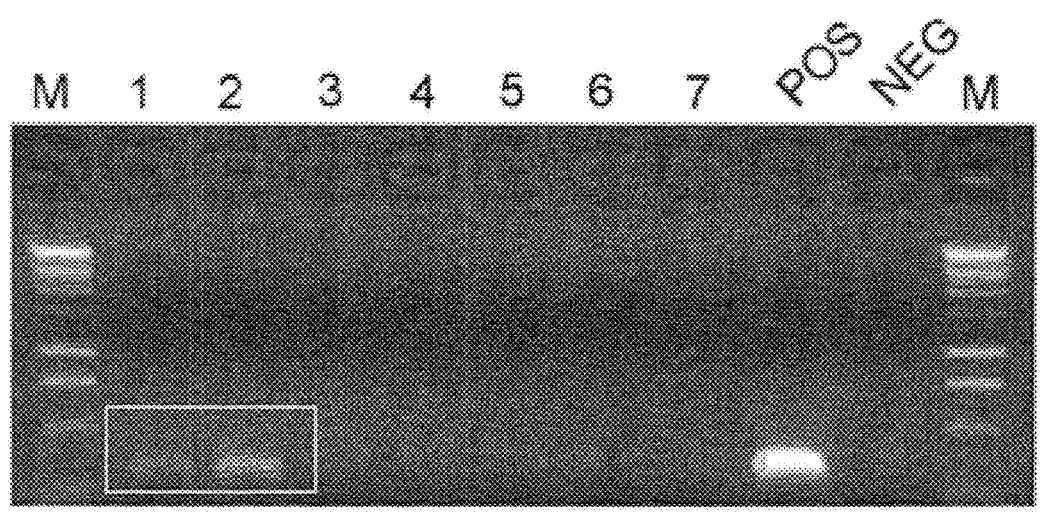
FIG. 7 shows the expression of SSX-2 in prostate cancer metastatic tissues. Prostate cancer metastatic tissue cDNA samples of 7 different prostate cancer patients (lanes 1-7) were analyzed for SSX-2 expression using PCR. Patients 1 and 2 showed relatively strong expression and patients 6 and 7 showed weak expression. POS and NEG are positive and negative controls, respectively. M represents molecular weight markers.

Using RT-PCR and SSX-2 specific antibody, the inventors found that SSX-2 was expressed in at least three prostate cancer cell lines: LAPC4 (FIG. 6), MDAPCa2b (FIG. 6), and LNCap (data not shown). The inventors also found that SSX-2 was expressed in prostate cancer metastatic tissue samples (FIG. 7).

TABLE 4

Antigen-specific IgG Responses

| Antigen | Patients with Prostate Cancer | Control Male Blood Donors |
|---|---|---|
| SSX-2 | 1/100 | 0/50 |
| NY-ESO-1 | 3/100 | 0/50 |
| MAD-Pro-22 | 16/100 | 9/64 |
| (PSA) | 22/200 by ELISA | 3/100 by ELISA |
| MAD-Pro-30 | 18/100 | 3/64 |
| MAD-Pro-34 | 5/100 | 0/64 |
| MAD-Pro-42 | 5/100 | 0/64 |
| MAD-CaP-1 | 2/100 | 0/50 |
| MAD-CaP-5 | 5/100 | 1/50 |
| MAD-CaP-15 | 3/100 | 0/50 |
| MAD-CaP-20 | 5/100 | 1/50 |
| MAD-CT-1 | 5/109 | 1/52 |
| MAD-CT-2 | 3/109 | 0/52 |
| MAD-CT-3 | 2/109 | 0/52 |
| MAD-CT-5 | 5/109 | 1/52 |
| Transgelin | 2/27 | 0/25 |
| ZCWCC3 | 5/26 | 4/25 |
| ACAA1 | 13/26 | 9/25 |
| AR LBD | 18/105 by ELISA | 0/41 by ELISA |
| Actinin | 1/1 | |

Although the invention has been described in connection with specific embodiments, it is understood that the invention is not limited to such specific embodiments but encompasses all such modifications and variations apparent to a skilled artisan that fall within the scope of the appended claims.

We claim:

1. A kit comprising:

a first polypeptide that comprises MAD-Pro-30 (SEQ ID NO: 58);

a second polypeptide that comprises androgen receptor (AR) ligand binding domain (SEQ ID NO: 59); and a third polypeptide that comprises MAD-Pro-22 (PSA) (SEQ ID NO: 57).

* * * * *